United States Patent [19]

Giebel et al.

[11] Patent Number: 5,433,705
[45] Date of Patent: Jul. 18, 1995

[54] INFECTION-PREVENTING CATHETER ARRANGEMENT

[76] Inventors: Marion Giebel, D.-Schürmann-Str. 12, 5630 Remscheid 1; Willehad Boemke, Düsseldorfer Str. 42, 1000 Berlin 15; Ülo Palm, Wilhelm-Tell-Str. 4/II, München 81677, all of Germany

[21] Appl. No.: 55,189

[22] Filed: Apr. 30, 1993

Related Application Data

[63] Continuation-in-part of PCT/DE90/00937, Nov. 2, 1990.

[51] Int. Cl.[6] ............................................. A61M 37/00
[52] U.S. Cl. ................................... 604/82; 604/87; 604/265
[58] Field of Search ......................... 604/264–265, 604/280, 27, 35, 36, 82–91, 93; 623/1, 11, 12

[56] References Cited

U.S. PATENT DOCUMENTS

| | | | |
|---|---|---|---|
| 4,693,706 | 9/1987 | Ennis | 604/87 |
| 4,879,135 | 11/1989 | Greco | 623/1 |
| 5,019,096 | 5/1991 | Fox | 604/265 |
| 5,019,378 | 5/1991 | Allen | 604/265 |
| 5,059,174 | 10/1991 | Vaillancourt | 604/82 |
| 5,061,255 | 10/1991 | Greenfeld | 604/265 |
| 5,112,301 | 5/1992 | Fenton | 604/247 |
| 5,127,904 | 7/1992 | Loo | 604/83 |
| 5,181,909 | 1/1993 | McFarlane | 604/87 |
| 5,181,913 | 1/1993 | Erlich | 604/247 |
| 5,224,938 | 7/1993 | Fenton | 604/247 |
| 5,261,885 | 11/1993 | Lui | 604/247 |
| 5,269,770 | 12/1993 | Conway | 604/265 |
| 5,290,228 | 3/1994 | Uemura et al. | 604/90 |
| 5,298,024 | 3/1994 | Richmond | 604/90 |

FOREIGN PATENT DOCUMENTS 0178023  4/1986  European Pat. Off. ............. 604/36

OTHER PUBLICATIONS

Publications: "Nosocomial Bacteremia–An Epidemiologic Overview", The American Journal of Medicine, Mar. 1981. Vol. 70.

"Anitbiotic-lock technique: a new approach to optimal therapy for Catheter-Related Sepsis in Home-Parenteral Nutrition Patients", vol. 12, No. 2, 1988.

Primary Examiner—C. Fred Rosenbaum
Assistant Examiner—Chalin Smith
Attorney, Agent, or Firm—Horst M. Kasper

[57] ABSTRACT

Anti-infection catheter arrangement comprising a catheter which has a rigid or flexible catheter tube with a connection piece at the distal end, characterized by a filling and suction device which can be attached to the connection piece and one or more active principle reservoirs with a total volume equal to the capacity of the catheter, possibly in addition the volume of intermediate pieces, in particular a three-way valve. This volume is entirely filled and at least one of the active principle reservoirs is filled with a substance containing at least an antibiotic agent or a chemotherapeutic agent or an antiviral agent, preferably aminoglycoside, in particular gentamycin, in at least a minimal effective concentration.

30 Claims, 3 Drawing Sheets

INFECTION-PREVENTING CATHETER ARRANGEMENT

CROSS-REFERENCE TO RELATED APPLICATIONS

This application is a continuation-in-part application of another international application filed under the Patent Cooperation Treaty Nov. 2, 1990, bearing Application No. PCT/DE90/00937, and listing the United States as a designated and/or elected country. The entire disclosure of this latter application, including the drawings thereof, is hereby incorporated in this application as if fully set forth herein.

BACKGROUND OF THE INVENTION

1. Field of the Invention

The invention relates to an infection-preventing catheter arrangement with a catheter which exhibits a rigid or flexible catheter tube with a connection piece furnished at the distal end of the catheter tube.

2. Brief Description of the Background of the Invention Including Prior Art

An important and frequently life-endangering complication in connection with the use of intravascular catheters comprises the occurrence of catheter-caused infections. The infection rate increases the longer the catheter remains in the body. For demonstrating the explosive importance of this problem, reference is made to a study, which is representative for a large number of similar investigations and which appeared in the "American Journal of Medicine" in 1981. According to this study, about 20,000 death cases occur each year in the United States, which death cases are attributed to catheter-caused infections. The research programs which have been performed and which are still currently being performed relative to this problem field worldwide are correspondingly numerous and varied.

It is known that pathogenic bacteria, once penetrated into the catheter, find ideal growth conditions there and they can uninhibitedly reproduce in an environment and under conditions of complete absence of antibodies, immune bodies or defense mechanisms present in the body. The result is a washing in of entire bacteria colonies into the body of the patient and thus causing a bacteriaemia, bacillaemia, or, respectively, sepsis, blood poisoning.

The past attempts to decrease the infection rate are substantially based on four different propositions, which have the goal, first to kill the bacteria, second to prevent access into the interior of the catheter to the germs, third to employ special catheter materials which make a bacteria invasion and bacteria appositioning more difficult, and fourth, combinations of these three methods.

Four United States patents are in particular to be noted with respect to the first proposition.

A catheter is described in the U.S. Pat. No. 4,623,329, where the catheter tube wall is furnished with capillaries containing germicidal agents. The agents pass by diffusion into the interior of the catheter. The effect which can be achieved in this manner, however, is very limited because the concentration of the agent is too low. In addition, the non-uniform release of the agents as well as the complicated construction of this special catheter are disadvantageous.

Technical solutions for closure cap systems with an agent reservoir or, respectively, an agent-absorbing wall material are known from the U.S. Pat. Nos. 4,432,764, 4,440,207, and 4,624,664. Said closure cap systems can be attached to the rearward connection piece during non-use of the catheter. Such closure caps fight however only a contamination of the catheter closure possibly occurring upon removal of the infusion tube and they do not fight the bacteria infiltrating through the catheter tube tip. It is known however, that an increasing deposit of bacteria occurs in particular at the tip of the catheter tube.

The second proposition is based on obtaining the goal to prevent bacteria from accessing the interior of the catheter tube. A duck-bill valve is known from the German Printed Patent Document DE-OS 35 04 661. This duck-bill valve allows the entrance of the medication or, respectively, of the solutions to be injected into the vessels as a one-way valve. On the other hand, however, the duck-bill valve prevents that liquids from the vessels can flow back into the catheter. One-way valves however are associated in principle with the disadvantage that the testing of the position of the catheter in a blood vessel is not possible based on an aspiration of blood.

It is furthermore conventional to insert a mandrin into the catheter tube in order to close the catheter tube during an intermittent injection. A catheter device with a mandrin is described in the German Printed Patent Document DE-OS 37 21 299. The medication, injected through an auxiliary injection port, flows through a fluid channel between mandrin and catheter tube and the medication exits through a valve from the catheter tube. Since the mandrin does not have to be removed any more from the catheter tube for an injection, a contamination of the lumen of the catheter tube is substantially avoided.

According to the proposals of the two precedingly recited German Printed Patent Documents, valves are employed which in fact prevent the infiltration of body liquid, but which do not prevent the infiltration of bacteria. A lack in sealing capacity and, in particular, the opening of the valve during the injection lead to the situation that some bacteria still pass into the catheter tube. However, already a few bacteria are sufficient to cause an infection danger.

A third possibility for decreasing the infection danger comprises to employ an antiseptic material for the catheter tube of the catheter or, respectively, to coat the catheter tube at least in part with such a material.

A bacteria-resisting mixture made of biocompatible base material and antibiotic metals is taught in the U.S. Pat. No. 4,677,143. It is proposed in the U.S. Pat. No. 4,642,104 to chemically bind an antimicrobic material to a base polymer. However, it has been shown in the clinical practice that more tissue damages, in particular irritations and inflammations, are caused by these catheters than by non-treated catheters. In addition, there exists the danger of development of a resistance by the bacteria against the antimicrobic metal.

A fourth method of approaching the problem is based on a combination of the above recited and discussed first three solution propositions.

Catheters or, respectively, additional units for catheters are described in the German Printed Patent Document DE-OS 37 47 548 and in the U.S. Pat. No. 4,676,782, which have the goal to prevent microbes from accessing through the implantation wounds, by employing locally antibiotics-containing materials. For this purpose, according to the German Printed Patent Document DE-OS 37 47 548, the outer surface of the catheter tube section, disposed in the region of the body opening, is furnished with a hydrophobic microbe-absorbing coating. The effect of the additional unit for arbitrarily commercially available catheters, described in the U.S. Pat. No. 4,676,782, is based on a similar principle, a separate sleeve for encasing the puncture region is proposed. This device, also known under the designation VITA CUFF, however, similar to the variant, described in the German Printed Patent Document has only a local effect and therefore brings only a partial success.

All conventionally known, above discussed measures for the decrease and the prevention of catheter-caused infections have so far only led to very small successes.

In addition, the injection of an antibiotic solution into the catheter is disadvantageous, where the injected volume is much larger than the catheter volume, as described in B. Messing, O. Peitra, A. Debure, M. Beliah, J. Bernier, entitled Antibiotic-Lock Technique: a new approach to optimal therapy for catheter-related sepsis in homeparenteral nutrition patients, J. Parenter Enteral Nutr. 1988; 12:185-189. Based on the penetration of the excessive antibiotic solution into the organism, the concentration of the antibiotic necessarily has to be kept so low that no toxic side effects or bacterial resistances can occur. This is associated with the result that the germicidal effect of the antibiotic solution remaining in the catheter between two injections, is insufficient to completely kill all bacteria adhering at the inner wall of the catheter.

The prevention of catheter-caused infections is further discussed in G. Palm, W. Boemke, H. W. Reinhardt in Journal "Der Anaesthesist," Vol. 38, 1989, Supplement 1, page 129.

SUMMARY OF THE INVENTION

1. Purpose of the Invention

It is an object of the present invention to provide a catheter arrangement, wherein the catheter-caused infection rate is drastically reduced.

It is a further object of the present invention to provide for a catheter arrangement which is easy and convenient to handle during routine operation.

These and other objects and advantages of the present invention will become evident from the description which follows.

2. Brief Description of the Invention

The present invention provides an infection-preventing catheter arrangement including a catheter tube having a rear end. A connection piece is furnished at the rear end of the catheter tube. A filling and suction device can be connected to the connection piece. The filling and suction device includes an active-agent reservoir with a total volume of at least a catheter filling volume. This total volume of the active-agent reservoir is completely filled. The active-agent reservoir is filled with a substance, containing an agent selected from the group consisting of antibiotic agents, chemotherapeutic agents, antiviral agents and mixtures thereof in at least a minimum active concentration.

The antibiotic agent can be aminoglycoside or gentamycin.

The total volume of the active-agent reservoir can be at least equal to the catheter filling volume plus the volume of intermediate pieces or the volume of a three-way valve.

The catheter tube can be rigid or the catheter tube can be flexible.

The agent selected from the group consisting of antibiotic agents, chemotherapeutic agents, antiviral agents and mixtures thereof can be present in a highest possible active concentration.

The substance can further contain at least one proteolytic enzyme, in particular protease, in particular alpha-chymotrypsin.

The active-agent reservoir can further contain an antimycotic agent. The active-agent reservoir can contain an anticoagulant.

The filling and suction device can be formed for suctioning at least the filling volume of the active-agent reservoir.

The filling and suction device can exhibit essentially a cylindrical shape. The first active-agent reservoir and a second active agent reservoir can be disposed sequentially in axial direction of the catheter arrangement. The first active-agent reservoir can be separated from the second active-agent reservoir by a membrane. The second active-agent reservoir can be disposed on the catheter side and can contain a proteolytic enzyme. The first active-agent reservoir can exhibit a tip closed with a membrane, where the tip can be adapted to the connection piece. A plunger can be disposed shiftable inside the first active-agent reservoir and the second active-agent reservoir. A shifting path of the plunger can correspond at least to an axial length of the first active-agent reservoir and of the second active-agent reservoir. The plunger can sealingly close with the wall of the first active-agent reservoir and of the second active-agent reservoir. A connection between the filling and suction device and the catheter can be formed as a Luer closure.

The filling and suction device can be formed of plastic. The plastic can be transparent. The filling and suction device can be furnished with a scaling corresponding to a shifting length of the plunger. A catheter can be formed essentially of a biocompatible material.

The catheter can be an indwelling catheter. The catheter can be made of polyurethane. The catheter can include a tube tip. The tube tip can exhibit means for closing the catheter tube opening.

Lamellae can be disposed in the catheter tube. Said lamellae can be moved like a swinging door in two directions, based on the injection pressure and the suction action, respectively.

The filling and suction device can be furnished for filling the catheter volume and the volume of a three-way valve disposed between the catheter and the filling and suction device.

The filling and suction device can be formed as a closed system. The filling and suction device can exhibit a removable protective cap.

A separate sterile packaging unit can be furnished for and can contain the filling and suction device. A sterile, separately packed closure cap can be attached to the filling and suction device.

A method for preventing infections in catheter operation comprises the following steps. A catheter tube is employed which has a rear end, and where a connection piece is furnished at the rear end of the catheter tube. A filling and suction device is employed which includes an active-agent reservoir with a total volume of at least a catheter filling volume and which is connectable to the connection piece. The active-agent reservoir of the filling and suction device is completely filled with a solution containing an agent selected from the group consisting of antibiotic agents, chemotherapeutic agents, antiviral agents and mixtures thereof in at least a minimum active concentration. A separate part of the catheter tube is flushed with the solution. The solution is removed from the separate part. The separate part is filled with an agent to be supplied to a patient.

At least the filling volume of the active agent reservoir is suctioned with the suctioning and filling device. The first active-agent reservoir is separated from a second active-agent reservoir by a membrane. The second active-agent reservoir is disposed on the catheter side and contains a proteolytic enzyme. A plunger is disposed shiftable inside the first active-agent reservoir and the second active-agent reservoir. A shifting path of the plunger corresponds at least to an axial length of the first active-agent reservoir and of the second active-agent reservoir. The plunger sealingly closes with a wall of the first active-agent reservoir and of the second active-agent reservoir. A connection between the filling and suction device and the catheter is formed as a Luer closure.

The invention is based on the results of extensive animal-experimental research, as reported by Ü. Palm, W. Boemke, H. W. Reinhardt, Prevention of Catheter-Caused Infections, An Experimental Long-Term Investigation, Anaesthesist, 1989, Vol. 38, Supplement 1, page 129. It has been found that, in case of dogs the catheter-caused infection rate of nearly 100% can be dropped to nearly 0%, where the catheter volume is intermittently filled with a highly concentrated gentamycin solution, to which some alpha-chymotrypsin is admixed.

According to the invention a special device, attachable to the rearward connection piece of the catheter, is furnished for the purpose to fill the catheter volume with at least one antibiotic-acting substance of at least a minimum effective concentration and to withdraw again at least the same volume. The filling volume corresponds thereby exactly to the catheter volume.

A further optimization of the intended effect can be achieved by an as high as possible concentration of the antibiotic. The antibiotic agent can additionally be enriched with proteolytic enzymes, in particular protease, and in particular alpha-chymotripsin. The pathogenic bacteria, penetrated into the catheter, for example, during the injection process, surround themselves during the formation of a colony with a protein shell, whereby the antibiotics in part can be shielded from the bacteria, which interferes with the efficiency of the effect of the antibiotics. It can be assumed that proteolytic enzymes destroy such protective shells so that the antibiotics can again be fully effective.

In case of certain catheter arrangements, it can be advantageous to add antimycotic agents for combatting pathogenic fungi and of anticoagulant, in particular of heparin for the prevention of blood clots and the thereby caused blockages of the catheter tube in case of certain catheter applications.

It is important that the substance is only active inside of the catheter and does not pass into the body of the patient. It is thereby assured that the highest possible concentration of the active agent can be employed while avoiding the otherwise occurring side effects and resistance developments. A filling and suction device with regard to this is characterized according to a preferred embodiment of the invention in that the suctioned volume exceeds slightly the catheter volume, whereas the filling volume corresponds exactly to the catheter volume. In this way, it is assured that no active-agent residues remain in the catheter and can penetrate into the body of the patient.

According to a particularly preferred embodiment of the invention the device is furnished with two separate substance reservoirs for alpha-chymotrypsin and gentamycin. Such a device exhibits preferably a cylindrical shape, wherein the substance reservoirs are disposed successively in an axial direction. The first reservoir on the catheter side contains the alpha-chymotrypsin. The two reservoirs are only separated by a thin membrane. This thin membrane can be easily destroyed for the purpose of mixing the two substances. The mixing of the powdery alpha-chymotrypsin with the liquid gentamycin, however, can only occur immediately preceding or during the filling process into the catheter, since the dissolved chymotrypsin develops its effect only during a short time period.

The connection piece of the filling and suction device is adapted to the connection piece of the catheter such that a sealing connection is assured. However, a broad standardization is possible since in particular Luer threads have been generally accepted for the catheter connections.

The two-chamber reservoir of the device for the agent is closed off by a second membrane toward the catheter opening. This membrane tears based on the pressure of a piston or plunger shiftable within the cylindrical reservoir, whereby simultaneously the gentamycin/chymotrypsin solution is pressed into the catheter. The plunger motion is particularly easy and safely with a cap, which can be screwed on to the outer wall of the device and where the cap is connected to the plunger. In the same manner, the plunger can be shifted in the opposite direction, for the suctioning of the active agent present in the catheter, wherein the restoring path slightly surpasses the starting position. This guarantees that not the smallest residue of the highly-concentrated antibiotic can be flushed into the body of the patient.

In order to submit the fluid, suctioned back into the device cylinder, to an analysis laboratory in a bacterially shielded state, there is furnished a sterile, separately packed closure cap. Such analyses serve for the purposes of controlling the freedom of bacteria. For example, fungi can be found in the catheter, protected against bacteria, whereby the use of a device containing an antifungal agent becomes necessary. The device is preferably furnished for single use. In case of single-chamber systems, which exhibit a valve suitable for passage in two directions instead of a membrane, however, a reusability is conceivable. A precondition for the re-use is furthermore a cleaning and a sterilization between two applications and the filling with a new active agent, wherein the enclosure of air bubbles is in particular to be avoided. Such an expenditure, however, is hardly justified in view of the simple construction of a single-chamber filling and suction device already for economic reasons.

The device is preferably made at least in its essential parts of a plastic material. A transparent plastic is in particular advantageous for the chamber(s), if a scaling, corresponding to the plunger displacement, is furnished. In general, the catheter volume is in fact constant such that the volume of the active-agent reservoir is already conceived to correspond to the catheter volume, whereby a scaling is not necessary. In an individual case, however, it can be necessary to shorten the catheter tube because of brittleness problems or because of mechanical damage. In this case, the decreased catheter volume can be balanced by a scaling of the filling volume.

According to a further feature of the invention, a three-way valve is disposed between the catheter and the device. This three-way valve allows two feed lines to be connected to the catheter connection piece, upon releasing a passage direction or upon closure in both directions. The volume to be filled is then composed of the filling volume of the catheter and of the inner volume of the three-way valve. The fact that the alternative connection of the infusion tube and the filling and suction device can be dispensed with, is of particular advantage in connection with this arrangement. The two systems are continuously connected with the catheter connection piece. The exchange of the two systems is reduced to a switching of the three-way valve. This is associated with a time saving as well as a further increase of the safety against contamination. The penetration of the gentamycin into the circulatory system should be avoided because of possible side effects, in particular feared are the nephrotoxicity and the ototoxicity and because of resistance development. A valve was therefore disposed at the tip of the catheter tube as an advantageous further feature of the invention. Advantageously, the valve is formed as a lamellae, which moves like a swinging door based on injection pressure or suction effect. The precedingly described arrangement of the catheter allows to drastically reduce or, respectively, to eliminate for good the danger of catheter-caused infections in human beings and animals. The ease of handling the filling and suction device allows the routine use and, in addition, the operation by medical auxiliary personnel or even by the patient himself or herself.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1A:
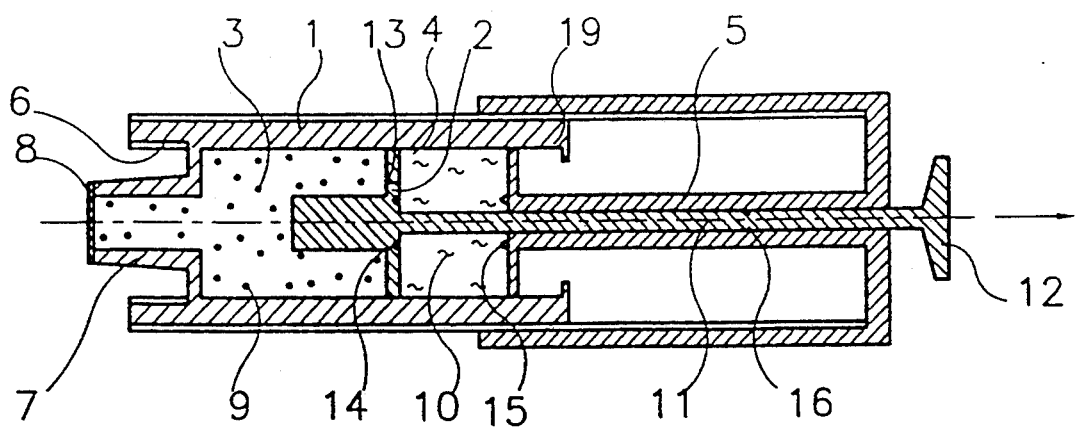
FIG. 1a is a sectional view of a first embodiment of a filling and suction device in a first application phase.

According to the present invention, there is provided for an infection-preventing catheter arrangement with a catheter, which exhibits a rigid or flexible catheter tube with a connection piece furnished at the rear end of the catheter tube. A filling and suction device 27 is connectable to the connection piece 32. The filling and suction device 27 includes at least one active-agent reservoir with a total volume corresponding to the catheter filling volume, possibly with the addition of the volume of intermediate pieces, in particular of a three-way valve. This volume is completely filled. At least one active-agent reservoir is filled with a substance, containing at least one antibiotic or, respectively, chemotherapeutic agents or, respectively, antiviral agent, preferably an antibiotic agent such as aminoglycoside, in particular gentamycin 10, in at least a minimum active concentration.

The antibiotic or, respectively, chemotherapeutic agent or, respectively, the antiviral agent can exhibit the highest possible active concentration. The substance can further contain at least one proteolytic enzyme, in particular protease, in particular alpha-chymotrypsin, an antimycotic agent, an anticoagulant, in particular heparin. The filling and suction device can be formed for suctioning at least the filling volume. The device can exhibit essentially a cylindrical shape. The active-agent reservoirs 3 and 4 can be disposed sequentially in axial direction of the catheter arrangement. The first active-agent reservoir 3 on the catheter side can contain an proteolytic enzyme, in particular alpha-chymotrypsin 9. The second active-agent reservoir 4 can contain the antibiotic agent or, respectively, the chemotherapeutic agent or, respectively, the antiviral agent, in particular gentamycin 10. The first active-agent reservoir 3 can be separated from the second active-agent reservoir 4 by a membrane 8, 22. The first active-agent reservoir 3 can exhibit a tip closed with a membrane 8. The tip can be adapted to the catheter connection piece 32. A plunger 5 or, respectively, 5′, shiftable inside the first active-agent reservoir 3 and the second active-agent reservoir 4, can be furnished, where a shifting path of the plunger 5 or, respectively, 5′, can correspond at least to the axial length of the first active-agent reservoir 3 and of the second active-agent reservoir 4. The plunger 5 or, respectively, 5′ can sealingly close with the wall of the first active-agent reservoir 3 and of the second active-agent reservoir 4.

The connection between the filling and suction device 27 and the catheter can be formed as a Luer closure 6. The filling and suction device 27 can be intended for disposable use. The filling and suction device 27 can essentially be made of plastic, in particular, transparent plastic. The filling and suction device 27 can be furnished with a scaling corresponding to the plunger shifting. A catheter 25 can be formed essentially of a biocompatible material, in particular polyurethane. The catheter 25 can be an indwelling catheter. The catheter can include a tube tip 36. The tube tip 36 can exhibit means for closing the catheter tube opening. Lamellae can be disposed in the catheter tube. Said lamellae can be moved like a swinging door in two directions, based on the injection pressure or, respectively, the suction action. The filling and suction device 27 can be furnished for the filling of the catheter volume and of the volume of a three-way valve 26 disposed between the catheter 25 and the filling and suction device 27. The filling and suction device 27 can be formed as a closed system. The filling and suction device can exhibit a removable protective cap. A separate sterile packaging unit can be furnished for and can contain the filling and suction device. A sterile, separately packed closure cap 21 can be attached to the filling and suction device 27.

The filling and suction device illustrated in FIG. 1a comprises essentially a cylindrical casing 1, a movable wall 2, where the movable wall subdivides the interior space into two axially successively disposed chambers 3 and 4, as well as a plunger 5, where the plunger 5 forms the front face boundary of the device on the side remote from the catheter. A Luer thread 6 and a plug cone 7 serve for connecting the catheter. A Luer thread includes a safety mechanism for a proper positioning and fixing of the cannulae. The plunger of a Luer syringe accurately fits and securely closes the barrel or cylinder. Furthermore, Luer syringes are accurate in measuring medication for administration and they are adaptable to the needs. The plug cone 7 is closed at its tip with a membrane 8. The first chamber, delimited by the membrane 8, the plug cone 7, a part of the cylindrical casing 1 and the movable wall 2, is filled with alphachymotripsin 9, whereas the second chamber 4, delimited by the movable wall 2, a further part of the casing 1, and the front face of the plunger 5, contains the antibiotic agent, chemotherapeutic agent or, respectively, antiviral agent.

Antibiotic agents include synthetic antibacterial agents, such as the sulfonamides and quinolones and are defined in Goodman & Gilman's The Pharmacological Basis of Therapeutics, 8th Edition, Volume II (1991), Pergamon Press, N.Y., Oxford, Beijing et al., p. 1034.

Chemotherapeutical agents are low molecular compounds capable of substantial and selective damage to germs causing sickness and cells of tumors and are defined in Pschurembel Klinisches Wörterbuch, Walter de Gruyter, Berlin, N.Y. (1986), page 269.

The antibiotic agents preferably employed are aminoglycocides such as gentamycin.

Additionally, the second chamber can contain a proteolytic enzyme and in particular a protease such as alphachymotrypsin. The proteolytic enzymes are defined for example in Rapoport, S. M. and H. J. Raderecht, Physiologisch-chemisches Praktikum, 7th Edition, 1977, VEB Verlag Volk und Gesundheit, Berlin, page 325, and in Stryer, Lubert, Biochemistry, 2nd Edition (1981), W. H. Freeman and Company, San Francisco, page 26.

The second chamber can further contain an antimicrobial agent such as chlorobutanol, benzylalcohol, and chlorocresol such as discussed in S. Lemmen, A. Kropec, V. Frank, F. Daschner in "In-vitro Untersuchungen zur Therapie yon Katheterinfekt. mit der Antibiotikum-Lock-Technik" published in the Journal "Intensivmedizin und Notfallmedizin," Volume 29, Issue 8 (1992).

Furthermore, antimycotic agents can be present such as amphotericin B, nystatin, griseofulvin, clotrimazole, 5-fluorocytosine, as defined in Pschyrembel, Klinisches Wörterbuch, Walter de Gruyter, Berlin, N.Y. (1986), page 94.

An anticoagulant can be contained in the second chamber such as anticoagulant drugs, thrombolytic drugs, and antiplatelet drugs, as defined in Goodman & Gilman's, The Pharmacological Basis of Therapeutics, 8th Edition, Volume II (1991), Pergamon Press, N.Y., Oxford, Beijing et al., page 1311, and in particular such as heparin, soluble salts of oxalic acid, citric acid, and hydrofluoric acid and as defined in Pschyrembel, Klinisches Wörterbuch, Walter de Gruyter, Berlin, N.Y. (1986), page 92.

The amount of agent contained in the second chamber will depend on the concentration commercially available, on the solubility of the agent and, in particular, of the antibiotic, on possible interferences of the antibiotic with the surface of the catheter, and on toxic or other effects that would result in cases where the volume or parts of the volume of the second chamber were inadvertently flushed into the circulation. The materials contained in the second chamber should be biocompatible, i.e. they should not or only insignificantly interfere with blood cells or tissue, in particular, they should not contribute to clotting, destruction of blood cells, infection, strong tissue reaction. The concentration of these agents can be a minimum inhibitory concentration as defined in Goodman & Gilman's, The Pharmacological Basis of Therapeutics, 8th Edition, Volume II (1991), Pergamon Press, N.Y., Oxford, Beijing et al., page 1018–1019.

This two-chamber system forms a closed unit, which is present completely sterile in a corresponding packaging unit, not illustrated, with a protective cap 21 also not illustrated for the membrane 8.

Figure 1B:
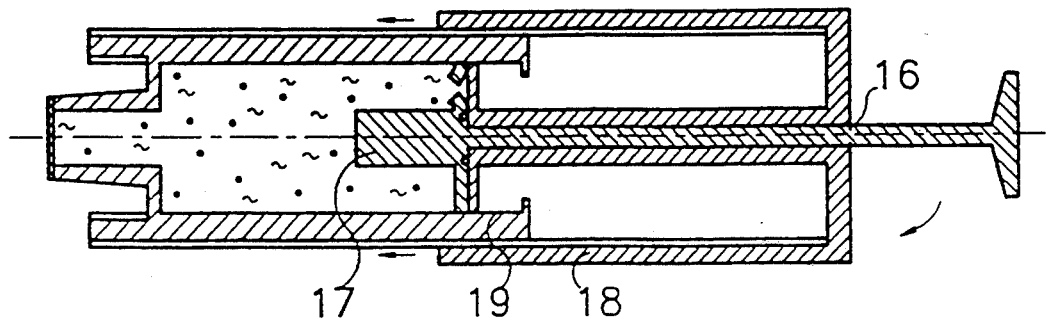
FIG. 1b is a sectional view of the first embodiment of a filling and suction device of FIG. 1 in a second application phase.
Figure 1C:
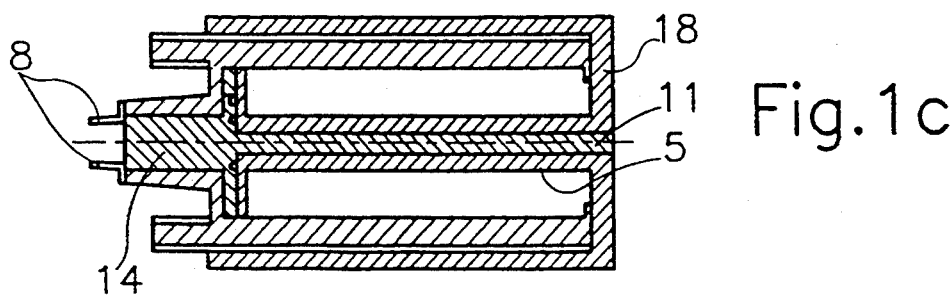
FIG. 1c is a sectional view of the first embodiment of a filling and suction device of FIG. 1 in a third application phase.
Figure 1D:
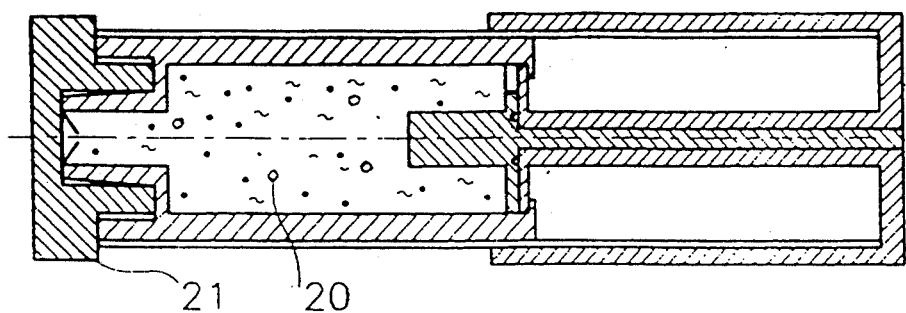
FIG. 1d is a sectional view of the first embodiment of a filling and suction device of FIG. 1 in a fourth application phase.

The protective cap 21, which is attached at the Luer thread 6 of the device, is removed immediately prior to the connection to the catheter, in order to avoid as much as possible a contamination of the connection piece, in particular of the membrane 8 by the bacteria continuously present in the air. The wall 2 can be pulled by a pull rod 11, where the pull rod 11 is axially lead through the body of the plunger 5, and where the pull rod 11 is furnished with a gripper 12 for the purpose of mixing the two substances, whereby a prescored, breaking point 13 of the wall 2 is torn. In the completely withdrawn state, an annular groove 14 at the rear side of the wall 2 engages into a corresponding annular collar 15 at the plunger front face. The pull rod 11 is furnished with a breaking point 16, whereby the gripper end can be broken off after the mixing process. The withdrawn position is illustrated in FIG. 1b. The alpha chymotrypsin/gentamycin solution now present in the complete reservoir can be pressed by plunger 5 into the catheter. The front face of the plunger 5 is formed by the movable wall 2. The wall 2 is therefore furnished with a projection 17, where the projection 17 is adapted to the interior space of the plug cone. Such a projection 17 is in fact not absolutely necessary for the functioning of the device, however, the total volume of the chambers 3 and 4 is to be increased by the volume of the inner space of the cone in case of elimination of the projection 17. The plunger 5 can be screwed with a screw cap 18 into the cylinder. The screw cap 18 can also be formed as a separate, plug cap, performing a translatory plunger motion for effecting opening and closing. FIG. 1c shows the device after filling the active-agent into the catheter. The membrane 8 is destroyed by the plunger pressure. The length of the device amounts in conventional catheter sizes to a maximum of several centimeters, such as 10 cm and preferably 5 cm, and the diameter is several millimeters, such as 10 mm and preferably 5 mm, such that the additional load is minimal for the patient. The antibiotic solution can be suctioned back into the reservoir of the device by screwing back the cap 18. The screw-back path is increased by the passage or fit length designated with the reference numeral 19 in the FIG. 1a and 1b, relative to the screw-in path. Consequently, some body liquid beyond the pure filling volume is sucked out of the catheterized hollow space, in particular, blood 20 (FIG. 1d). It is thereby assured that no active-agent residues of the flushing and sterilizing remain in the catheter, which could be washed into the body of the patient by a subsequent infusion. After the suction process, the device can in addition serve for the transfer of the suctioned fluid to a laboratory, in order to be investigated in the laboratory, for example, with respect to its content of bacteria. For this purpose, the filling and the suction device is closed with a sterile cap 21 immediately after the disconnection from the catheter, as can be seen in FIG. 1d.

Figure 2:
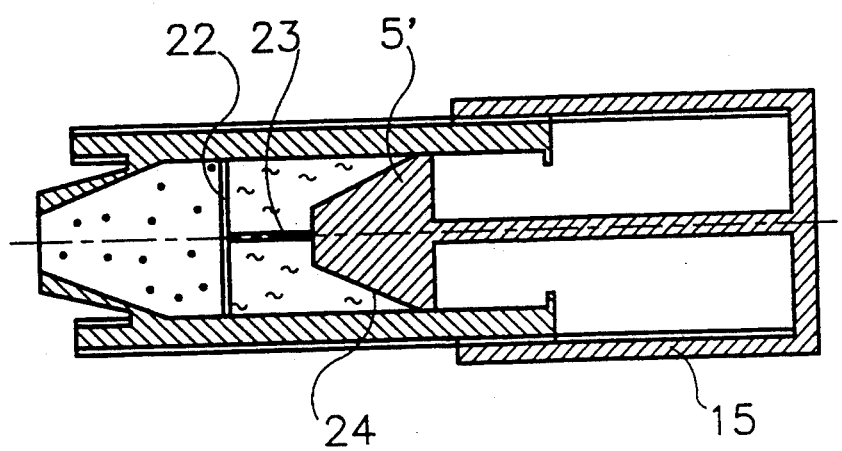
FIG. 2 is a sectional view of a second embodiment of a filling and suction device in a sectional view.

FIG. 2 shows a second embodiment of a two-chamber filling and suction device. The movable wall 2 of the first embodiment is in this case transformed into a thin membrane 22, where the thin membrane 22 is destroyed by a needle 23, moving together with the plunger 5'. The cylindrical shape of the reservoir, disposed on the side of the catheter, is furnished with a conical tip, which has the consequence that the cylinder-shaped projection 17 of the movable wall 2 is substituted by a truncated cone-like projection 24 of the plunger 5'.

Figure 3:
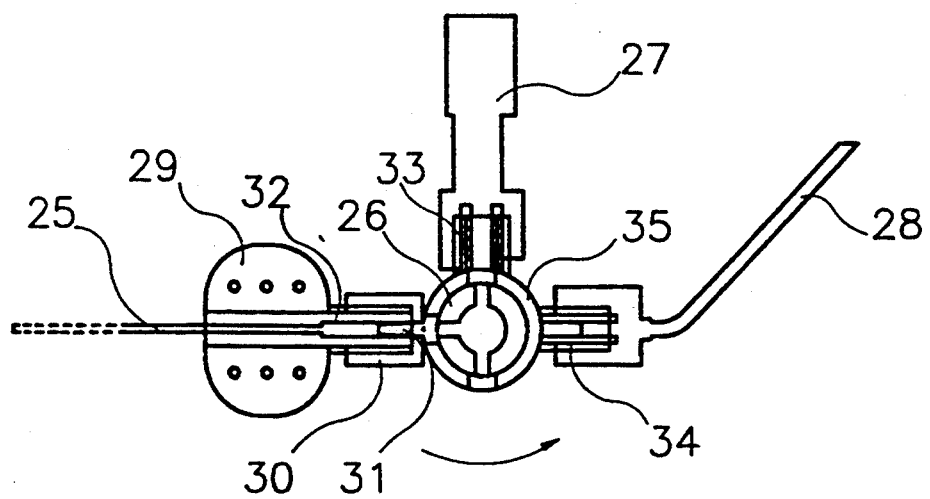
FIG. 3 is a sectional view of a filling and suction device including a three-way valve.

FIG. 3 shows an embodiment of an infection-preventing catheter arrangement with a catheter 25, a three-way valve 26, a filling and suction device 27, and an infusion tube 28, which leads to a container for the infusion liquid not illustrated. The catheter 25 is furnished at its connection side end on two sides with wings 29, which can be affixed to the skin with adhesive bandages. The three-way valve 26 exhibits a Luer screw cap 30 and a plug cone 31 for connection to the catheter exit port 32 as well as two Luer thread exit ports 33 and 34. The exit ports 33 and 34 are connected to a filling and a suction device 27 or, respectively, the infusion tube 28. It can be recognized that an open flow direction exists between the device 27 and the catheter 25 in the position illustrated, whereas the infusion tube 28 is separated from the catheter 25. If the outer ring 35 of the three-way valve 26 is rotated with a gripper, not illustrated, by 90 degrees in arrow direction, the flow direction between the infusion tube and the catheter 25 is opened and the connection between the filling and suction device 27 and the catheter 25 is closed. In this way, a quick switching to infusion is possible after removal of the catheter filling by the filling and suction device 27. Both the infusion tube 28 as well as the device 27 remain connected to the catheter exit port 32, whereby the changing of the connections can be dispensed with. The filling volume of the filling and suction device 27 is increased by the interior volume of the three-way valve 26.

Figure 4:
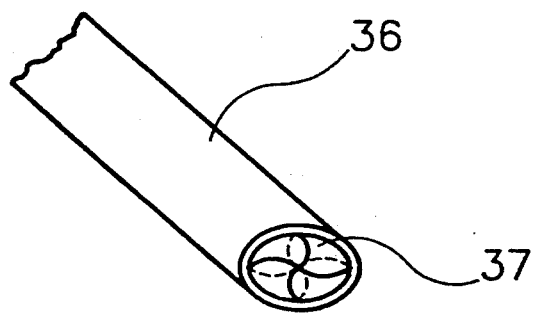
FIG. 4 a perspective view of a catheter-tube closure.

A variant for the valve-like closure of the catheter-tube tip 36 is illustrated in FIG. 4. Several lamellae 37, which are connected to the wall of the catheter-tube tip 36, overlap each other like an iris diaphragm, whereby a stable and reliably sealing closure of the catheter-tube tip 36 results in case of balanced pressure situations. The opening of the closure is possible in alike manner in the two directions in case of pressure effect or, respectively, suction effect. Based on the mutual overlapping of the lamellae 37, there is present a springing restoring force, where the springing restoring force guarantees a quick and exact closure also after frequent opening.

The invention is not restricted in its use to the precedingly recited preferred embodiment. On the contrary, a number of variants is conceivable, which make use of the represented solution even in case of embodiments which are in principle of a different kind.

It will be understood that each of the elements described above, or two or more together, may also find a useful application in other types of catheter arrangements differing from the types described above.

While the invention has been illustrated and described as embodied in the context of an infection-preventing catheter arrangement, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An infection-preventing catheter arrangement comprising
    a catheter tube having a rear end;
    a connection piece furnished at the rear end of the catheter tube and forming an intermediate piece;
    a filling and suction device connectable to the connection piece, wherein the filling and suction device includes an active-agent reservoir with a total volume of from about a catheter filling volume to the catheter filling volume plus a volume of any intermediate pieces wherein this total volume of the active-agent reservoir is completely filled with a substance, and wherein the substance contains an agent selected from the group consisting of antibiotic agents, chemotherapeutic agents, antiviral agents and mixtures thereof in at least a minimum active concentration.

2. The infection-preventing catheter arrangement according to claim 1, wherein the antibiotic agent is aminoglycoside.

3. The infection-preventing catheter arrangement according to claim 2, wherein the antibiotic agent is gentamycin.

4. The infection-preventing catheter arrangement according to claim 1, wherein the connection piece is a three-way valve disposed between the catheter tube and the filling and suction device, and wherein the total volume of the active-agent reservoir is equal to from about the catheter filling volume to the catheter filling volume plus a volume of the three-way valve.

5. The infection-preventing catheter arrangement according to claim 1, wherein the catheter tube is rigid.

6. The infection-preventing catheter arrangement according to claim 1, wherein the catheter tube is flexible.

7. The infection-preventing catheter arrangement according to claim 1, wherein the agent is present in a highest possible active concentration.

8. The infection-preventing catheter arrangement according to claim 1, wherein the substance further contains at least one proteolytic enzyme.

9. The infection-preventing catheter arrangement according to claim 1, wherein the substance further contains an antimycotic agent.

10. The infection-preventing catheter arrangement according to claim 1, wherein the substance further contains an anticoagulant.

11. The infection-preventing catheter arrangement according to claim 1, wherein the filling and suction device is formed capable of suctioning at least the volume of the active-agent reservoir.

12. The infection-preventing catheter arrangement according to claim 1, wherein the filling and suction device is formed of plastic;
wherein the plastic is transparent;
further comprising
a plunger disposed in the filling and suction device, wherein the filling and suction device is furnished with a scaling corresponding to a shifting length of the plunger;
a catheter formed essentially of a biocompatible material.

13. The infection-preventing catheter arrangement according to claim 1, wherein the filling and suction device is formed as a closed system; and
wherein the filling and suction device exhibits a removable protective cap.

14. The infection-preventing catheter arrangement according to claim 1, further comprising
a separate sterile packaging unit furnished for and containing the filling and suction device;and
a sterile,separately packed closure cap attachable to the filling and suction device.

15. The infection-preventing catheter arrangement according to claim 1, wherein the active-agent reservoir comprises a first active-agent reservoir and a second active-agent reservoir, wherein the filling and suction device exhibits essentially a cylindrical shape, and wherein the first active-agent reservoir and the second active agent reservoir are disposed sequentially in axial direction of the catheter arrangement.

16. The infection-preventing catheter arrangement according to claim 15 further comprising
a membrane, wherein the first active-agent reservoir is separated from the second active-agent reservoir by the membrane, and wherein the first active-agent reservoir is disposed on the catheter side and contains a proteolytic enzyme.

17. The infection-preventing catheter arrangement according to claim 16, wherein the first active-agent reservoir exhibits a tip closed with a membrane, wherein said tip mates with the connection piece.

18. The infection-preventing catheter arrangement according to claim 17, further comprising
a plunger disposed shiftable inside the first active-agent reservoir and the second active-agent reservoir, wherein a shifting path of the plunger corresponds at least to an axial length of the first active-agent reservoir and of the second active-agent reservoir, and wherein the plunger sealingly closes with a wall of the first active-agent reservoir and of the second active-agent reservoir, and wherein a connection between the filling and suction device and the mating tip is formed as a Luer closure.

19. The infection-preventing catheter arrangement according to claim 1, wherein the catheter is an indwelling catheter, and wherein the catheter is made of polyurethane, and wherein the catheter includes a tube tip, and wherein the tube tip exhibits means for closing an opening of the catheter tube.

20. The infection-preventing catheter arrangement according to claim 19, further comprising lamellae disposed in the catheter tube, which lamellae are movable like a swinging door in two directions,based on the injection pressure and the suction action, respectively.

21. An infection-preventing catheter arrangement with a catheter, which exhibits a rigid or flexible catheter tube with a connection piece comprising a three-way valve furnished at the rear end of the catheter tube,
wherein a filling and suction device (27) is connectable to the connection piece (32), wherein the filling and suction device (27) includes at least one active-agent reservoir (3, 4) with a total volume corresponding to from about a catheter filling volume to the catheter filling volume plus the volume of any connection piece, wherein this total volume is completely filled, and wherein at least one active-agent reservoir (3, 4) is filled with a substance, containing a first active agent selected from the group of one antibiotic agent, antiviral agent, and mixtures thereof, present in at least a minimum active concentration.

22. The infection-preventing catheter arrangement according to claim 21, further comprising a three-way valve, wherein a connection between the filling and suction device (27) and the three-way valve is formed as a Luer closure (6);
wherein the filling and suction device (27) comprises essentially plastic;
wherein the filling and suction device (27) exhibits a scaling corresponding to a shifting path of a plunger (5 or, respectively 5');
wherein the catheter (25) is formed essentially of a biocompatible material, in particular polyurethane, wherein the catheter (25) is an indwelling catheter, wherein the catheter (25) includes a tube tip (36), and wherein the tube tip (36) exhibits means for closing an opening of the catheter tube;
further comprising lamellae (37) disposed in the catheter tube, which lamellae (37) are movable like a swinging door in two directions, based on an injection pressure or, respectively, a suction action,
wherein the filling and suction device (27) is a closed system.

23. The infection-preventing catheter arrangement according to claim 21, wherein the agent is present in a highest possible active concentration;
wherein the substance further contains at least a second active agent of the group consisting of one proteolytic enzyme, capable of suctioning at least the total volume; and further comprising
a second active-agent reservoir (4);
wherein the device (27) exhibits essentially a cylindrical shape, and wherein the active-agent reservoirs (3 and 4) are disposed sequentially in axial direction of the catheter arrangement;
wherein the first active-agent reservoir (3) is disposed on a side of the catheter and contains the second active agent and wherein the second active-agent reservoir (4) is disposed neighboring to the first active-agent reservoir and contains the first active agent;
wherein the first active-agent reservoir (3) is separated from the second active-agent reservoir (4) by a membrane (22);
wherein the first active-agent reservoir (3) exhibits a tip closed with a membrane (8), where the tip mates with the connection piece (32);

wherein the catheter further comprises a plunger (5 or, respectively 5'), shiftable inside the first active-agent reservoir (3) and the second active-agent reservoir (4), wherein a shifting path of the plunger (5 or, respectively, 5'), corresponds at least to an axial length of the first active-agent reservoir (3) plus the second active-agent reservoir (4), and wherein the plunger (5 or, respectively, 5') sealingly closes with a wall of the first active-agent reservoir (3) and of the second active-agent reservoir (4).

24. The infection-preventing catheter arrangement according to claim 23, wherein the proteolytic enzyme is protease.

25. The infection-preventing catheter arrangement according to claim 24, wherein the protease is alpha-chymotrypsin.

26. The infection-preventing catheter arrangement according to claim 21, wherein the antibiotic agent is aminoglycoiside.

27. The infection-preventing catheter arrangement according to claim 26, wherein the aminoglycoside is a gentamycin.

28. A method for preventing infection in catheter operation comprising employing a catheter tube having a rear end and having a connection piece furnished at the rear end of the catheter tube;

employing a filling and suction device including an active-agent reservoir with a total volume of from about a catheter tube filling volume to the catheter tube filling volume plus the volume of the connection piece and connectable to the connection piece, wherein the active-agent reservoir of the filling and suction device is completely filled with a solution containing an agent selected from the group consisting of antibiotic agents, chemotherapeutic agents, antiviral agents and mixtures thereof in at least a minimum active concentration; maintaining the catheter tube with the solution when an agent to be supplied to a patient is absent;

suctioning at least the solution from the catheter tube, before an infusion of the agent begins.

29. The infection-preventing catheter arrangement according to claim 23, wherein the anticoagulant is heparin.

30. The infection-preventing catheter arrangement according to claim 22, where the closed system is formed as a kit including a removable protective cap, a separate sterile packaging unit containing the filling and suction device, and a sterile, separately packed closure cap (21) attachable to the filling and suction device (27).

* * * * *